United States Patent [19]

Wiltshire

[11] Patent Number: 5,564,446
[45] Date of Patent: Oct. 15, 1996

[54] DENTAL FLOSS DEVICE AND APPLICATOR ASSEMBLY

[76] Inventor: Curtis B. Wiltshire, 11 Nomas La., Richmond, Va. 23233

[21] Appl. No.: 411,503

[22] Filed: Mar. 27, 1995

[51] Int. Cl.⁶ ..................................................... A61C 15/00
[52] U.S. Cl. .......................................... 132/323; 132/309
[58] Field of Search ..................................... 132/321, 323, 132/324, 325, 326, 329, 309, 328

[56] References Cited

U.S. PATENT DOCUMENTS

| | | |
|---|---|---|
| 4,050,470 | 9/1977 | Miller . |
| 4,403,625 | 9/1983 | Sanders et al. . |
| 4,638,824 | 1/1987 | De La Hoz . |
| 4,655,233 | 4/1987 | Laughlin ................................. 132/323 |
| 4,890,732 | 1/1990 | Shackelford ........................... 132/309 |
| 4,941,488 | 7/1990 | Marxer et al. ......................... 132/323 |
| 5,067,503 | 11/1991 | Stile ....................................... 132/323 |
| 5,224,501 | 7/1993 | McKenzie . |
| 5,279,315 | 1/1994 | Huang . |
| 5,435,330 | 7/1995 | Dix ........................................ 132/323 |

FOREIGN PATENT DOCUMENTS 8807354  10/1988  WIPO .................................... 132/323

*Primary Examiner*—Cary E. O'Connor
*Attorney, Agent, or Firm*—J. Michael Martinez de Andino

[57] ABSTRACT

A dental floss device and applicator assembly comprising a pair of separate, substantially elongate members with each member having spaced apart top and bottom end portions with a gripping section located between the top and bottom end portions, a plurality of dental floss segments, and a slot formed in the top end portion of each member that has a prong protruding from the slot for releasably holding one of the dental floss segments (STRAND) within the slot. An alignment channel or groove can also be formed in the top end portion and located adjacent to the slot to hold and guide the STRAND within the alignment channel or groove without requiring a user to manipulate the STRAND with the user's fingers as the prong engages and holds the STRAND under the prong. The members are of sufficient length to allow a user to insert the members into a person's mouth with the STRAND attached to the top end portion of the members to clean all surfaces of the person's teeth without requiring the user to insert the user's fingers into the person's mouth. Further, the user does not have to manipulate the STRAND with the user's fingers when cleaning the person's teeth. The dental floss device and applicator assembly can also include a kit for storing the members and a container of dental floss segments.

21 Claims, 5 Drawing Sheets

5,564,446

DENTAL FLOSS DEVICE AND APPLICATOR ASSEMBLY

BACKGROUND OF THE INVENTION

1. Field of the Invention

This invention relates to the field of dental hygiene and, more specifically, to an improved dental floss device and applicator assembly for flossing the teeth.

2. Background Information

Conventional methods employed to floss the teeth encounter several problems. One such problem is the inability to easily hold dental floss without getting one's fingers and hands wet, cutting off the blood circulation in the fingers, or being able to reach the teeth far back into the mouth. A variety of devices have been suggested in the prior art to facilitate the handling of dental floss to remove food particles, plaque, and tartar from teeth. Dental floss is normally held in the hands and moved by the fingers to insert the dental floss in between two adjacent teeth. Prior art devices, such as the Miller U.S. Pat. No. 4,050,470 the Sanders et al. U.S. Pat. No. 4,403,625, the De La Hoz U.S. Pat. No. 4,638,824, the McKenzie U.S. Pat. No. 5,224,501, and the Haung U.S. Pat. No. 5,279,315 have suggested various ways for using dental floss.

The Miller '070 patent discloses a dental floss holder and applicator assembly that uses handles which have a strand of dental floss secured to the handles through the use of a slot that extends the length of the handles. The Sanders '625 patent discloses a disposable buccal hygienic device that can be separated into two separate ends which are connected by a strand of dental floss. The De La Hoz '824 patent discloses a dental floss device that has two separate flat dental floss securing rings that are connected by a strand of dental floss. The McKenzie '501 patent discloses the use of a pair of separate handles connected to a loop of dental floss, which is attached to the handles by either looping and gluing the strands of floss through holes located at the end of each handle, or by tying or stapling the floss strand ends to the handles. The Haung '315 patent discloses a dental floss assembly having a holder portion having a chamber for storing dental floss, a locating member mounted on the holder portion, and a holding member that is mounted on the locating member, with the holding member having a strand of dental floss mounted thereon. The Huang '315 patent device includes the use of a pin to change the angle of the holding member with respect to the locating member.

Prior art devices, which include the above-mentioned, require the user to manually insert or attach the dental floss strand to the respective holder devices to allow the user to floss his or her teeth. Further, the prior art devices require the user to either dispose of the dental floss holder or to press down on the holder to change the angle of a dental floss holding member with respect to a locating member.

In order to overcome the above-mentioned defects there is a need for a dental floss device and applicator assembly that allows individuals to quickly and easily engage a strand of dental floss without having to manually tie or attach the strand to the device. There is also a need for a dental floss device and applicator assembly which includes two handles, with each handle having a connecting end that is pushed or stabbed against a dental floss strand to anchor and engage the dental floss strand in place allowing the user to insert the dental floss in place for cleaning the spaces between the teeth.

SUMMARY OF THE PRESENT INVENTION

Accordingly, it is the primary object of the present invention to provide a dental floss device and applicator assembly that engages a strand of dental floss for cleaning the spaces between the teeth.

It is a further object of this invention to provide a dental floss device and applicator assembly that allows the user to clean the spaces between the teeth without having to wrap the dental floss around their finger, or manually tie or attach the dental floss to a handle holding device.

It is another object of this invention to provide a dental floss device and applicator assembly that includes handles which allows a user to attach a strand of dental floss to the top end of the handles by pushing or stabbing the top end of the handles against the strand, which automatically engages the strand to the handle, without having to touch the dental floss.

It is another object of this invention to provide a dental floss device and applicator assembly that includes handles that engage a strand of dental floss for cleaning the spaces between the teeth without having to wrap the dental floss around their finger, or manually tie or attach the dental floss to a handle holding device, and which allows a user to attach a strand of dental floss to the top end of the handles by pushing or stabbing the top end of the handles against the strand, which automatically engages the strand to the handle.

Other objects and advantages of this invention will become apparent from the following description taken in connection, with the accompanying drawings wherein are set forth, by way of illustration and example, certain embodiments of this invention.

DETAILED DESCRIPTION OF THE PREFERRED EMBODIMENTS

Figure 1:
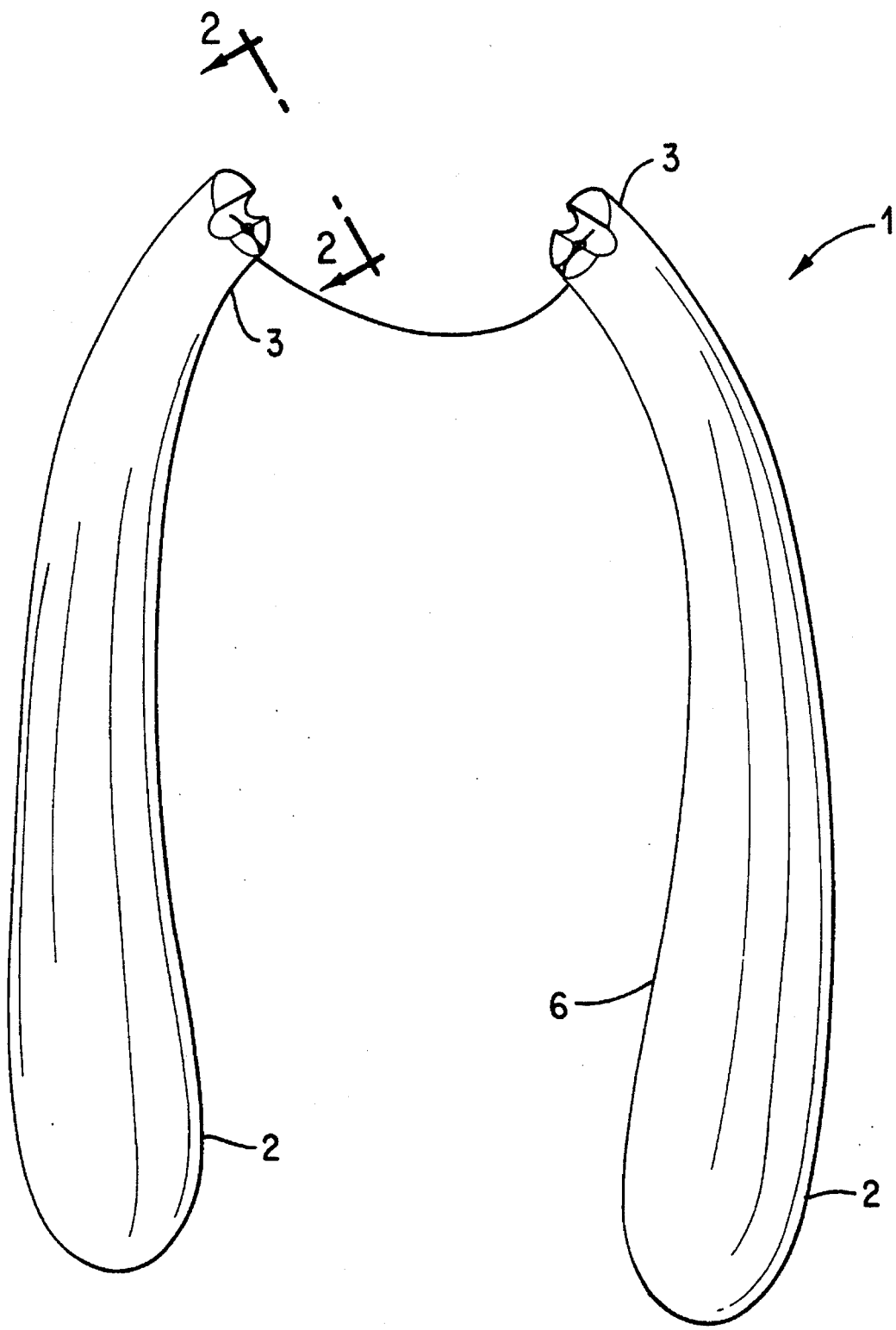
FIG. 1 is a side plan view of a typical embodiment of the invention showing the handle members of the dental floss device and applicator assembly.

Referring now to the drawings, a typical embodiment of the invention is shown in FIGS. 1–5. In this dental floss device and applicator assembly 1, a pair of handle members 2 are connected by a dental floss strand 5, such as a looped strand of dental floss, which preferably has a length of one to two inches. The members 2 are preferably made of plastic or flexible rubber, but can be made of almost any type of durable material. The members 2 have anatomically designed natural grips 6 and are approximately six inches in length.

Figure 2:
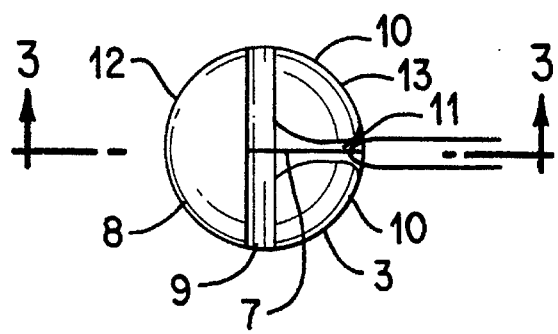
FIG. 2 is a top plan view of the top end of one of the handle members taken along lines 2—2 of FIG. 1, showing the engaging hook and the alignment guide.
Figure 3:
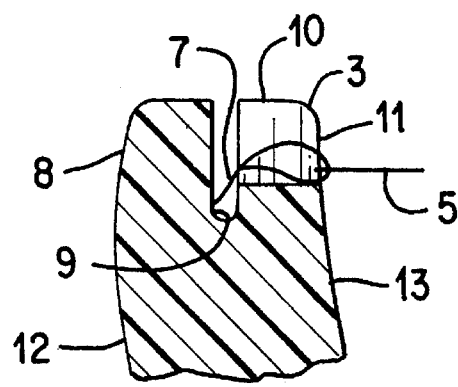
FIG. 3 is a side plan segment view of the top end of one of the handle members taken along lines 3—3 of FIG. 2, showing the engaging hook.
Figure 4:
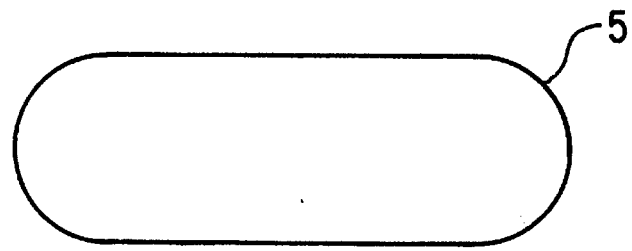
FIG. 4 is a top plan view of a dental floss loop strand.

The members 2 each have a top end 3, as shown in FIGS. 2 and 3, that is approximately ½ inch in diameter and designed to allow the engagement of the dental floss strand 5 with the top end 3 without strenuous effort and without having to touch the dental floss. The top end 3 has an engaging clip 7, an alignment guide 8, a channel 9, two clip guides 10 and a slot 11. The engaging clip 7 can be made of metal, plastic or other suitable material. The alignment guide 8 is adjacent to and integral with the non-working side 12 of the top end 3. The two clip guides 10, which are separated by the slot 11, are adjacent to and integral with the working side 13 of the top end 3. The channel 9 is formed by the slight separation between the alignment guide 8 and the two clip guides 10. The channel 9 forms a seat for receiving a portion of the dental floss strand 5 therein. The engaging clip 7 is attached to and mounted within the slot 11 and extends into and across the channel 9. The engaging clip 7 catches the dental floss strand 5 and keeps the dental floss strand 5 within the slot 11.

Figure 5:
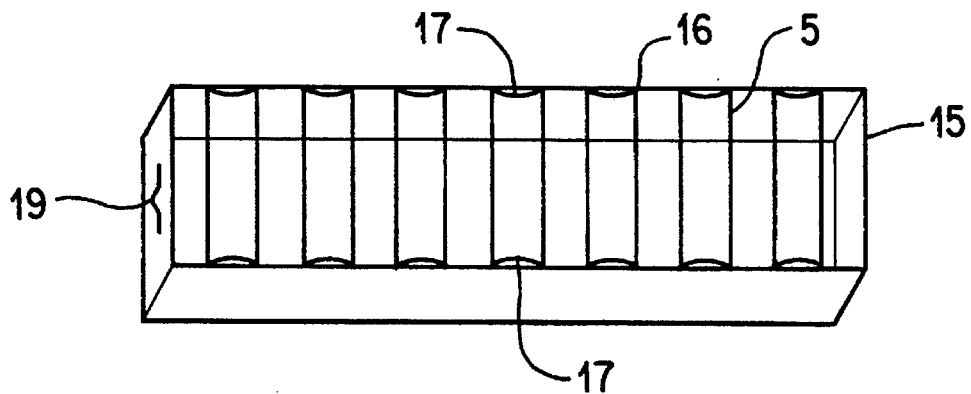
FIG. 5 is a perspective view of a container holding looped strands of dental floss.
Figure 6:
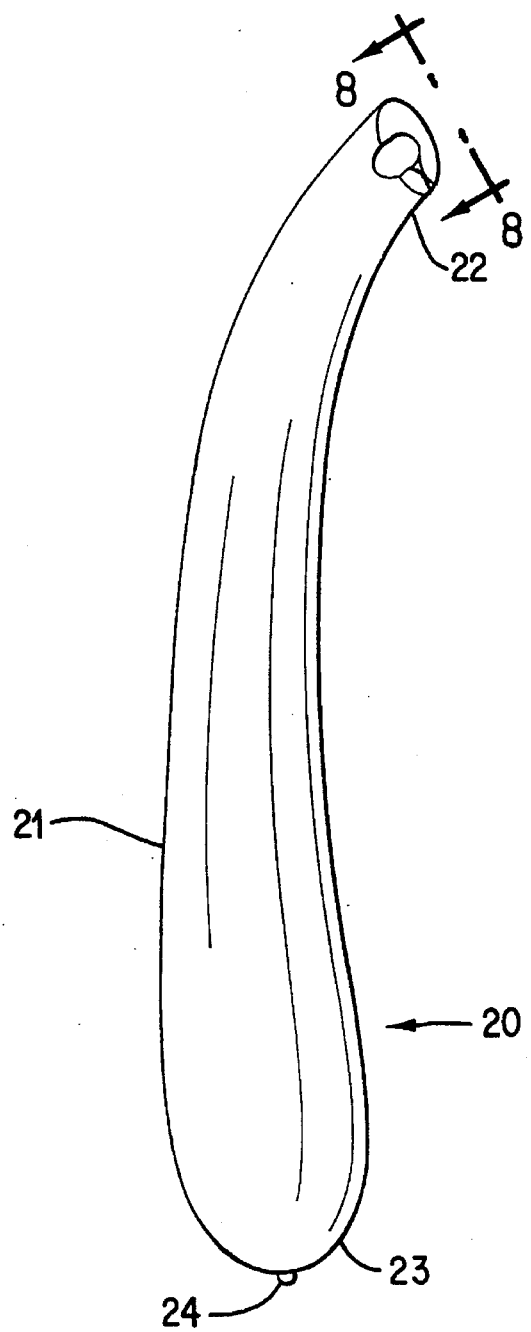
FIG. 6 is a side plan view of one of the handle members of a second embodiment of the invention in which the bottom end of the handle for the dental floss device and applicator assembly has an extricator.

As shown in FIG. 5, the dental floss strands 5 are stored in a container 15, which has support notches 16 located on the inner surfaces of sides 17 of the container 15. The notches 16 are spaced apart, preferably ¼ inch apart, for easy access by the user. The notches 16 are designed such that the dental floss strands 5 will easily slide off the notches 16 when the user takes the members 2, one in each hand, and pushes or stabs the top end 3 of the members 2 against the dental floss strands 5. The engaging clip 7 of each member 2 catches the dental floss strand 5 and allows the user to easily lift the dental floss strands out of the container 15. The user can then manipulate the members 2 into his or her mouth to have the dental floss strand 5 clean the spaces between the teeth.

The container 15 has a floss cutter 19 that allows the user to simply wipe the dental floss strand across the floss cutter 19 which cuts the dental floss strand 5. The floss cutter 19 is a slightly raised triangular wedge, which is attached to the outer surface of one of the ends of the container 15, but can be of any shape or design. The floss cutter 19 allows the user to remove the cut dental floss strand 5 (not shown) from the members 2. The user can then rinse the members 2 and store the members 2 for future use. The container 15 can be a component of a dental floss kit (not shown) which has storage room for the members 2 and for one or more container 15. Further, the kit can also have a floss cutter 19 attached thereto to facilitate in the removal of the dental floss strand 5 from the members 2.

As shown in FIG. 1, because the dental floss strand 5 is a continuous, circular piece of dental floss it is easy to be engaged by the top end 3 of the member 2, and allows the user to seemingly have a double strand of dental floss 18. The double strand of dental floss 18 is especially good for cleaning the spaces between the front teeth (not shown). As the user proceeds to clean the spaces of the posterior teeth, the user can twirl the members 2 three to five times to convert the double strand of dental floss 18 into a single stand which can facilitate the cleaning of the more rounded, bulbous contours that are found in the posterior teeth. After the teeth are cleaned, the user simply cuts the dental floss strand 5 by using the floss cutter 19. Referring now to FIGS. 6–11, a second embodiment of the invention is shown in this second embodiment of the dental floss design and applicator assembly 20, the invention includes a pair of handle members 21 that are connected by a single dental floss strand 25, which is preferably an inch to two inches in length. The members 21 are preferably made of plastic or flexible rubber, but can be made of almost any type of durable material. The members 21 have anatomically designed natural grips and are approximately six inches in length. The members 21 have a top end 22 and a bottom end 23, which has an extricator 24 attached thereto. The extricator 24 has a conical shape with a length of approximately ¼ inches.

Figure 7:
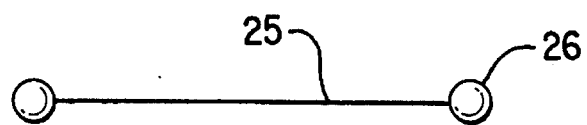
FIG. 7 is a side plan view of a single strand of dental floss.

As shown in FIG. 7, the single dental floss strand 25 has circular shaped anchors 26 attached to either end of the single dental floss strand 25. The anchors 26 are approximately ⅛ inch in diameter and are preferably made of plastic, although any durable and attachable material can be used to make the anchors 26.

Figure 8:
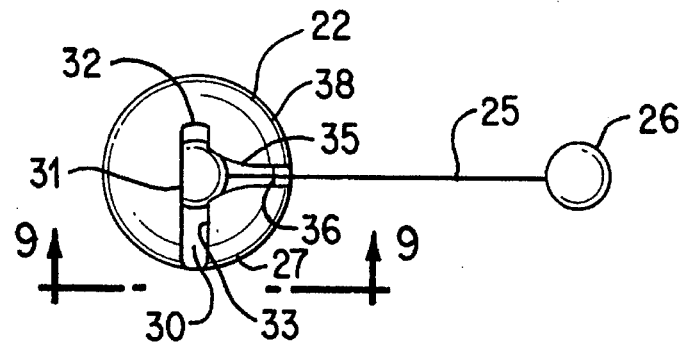
FIG. 8 is a top plan view of the top end of one of the handle members of the second embodiment taken along lines 8—8 of FIG. 6.
Figure 9:
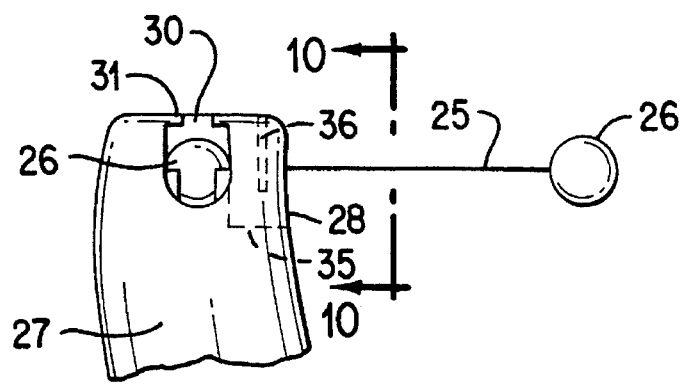
FIG. 9 is a side plan view of the top end of one of the handle members of the second embodiment taken along lines 9—9 of FIG. 8.
Figure 10:
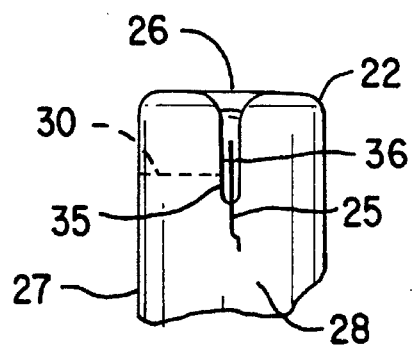
FIG. 10 is a side plan view of the top end of one of the members of the second embodiment taken along lines 10—10 of FIG. 9.

Referring to FIGS. 8–10, the top end 22 of one of the members 21 is shown with a single dental floss strand 25 connected thereto. The top end 22 has a connecting side 27 and a working side 28. The connecting side 27 has an attachment groove 30 that extends from the surface of the connecting side 27 to midway into the top end 22, and which has a height of approximately ⅜ inches. The attachment groove 30 has placement guards 31 which are located at and extend along the top edges of the attachment groove 30. The attachment groove 30 is designed to easily accommodate an anchor 26 by pushing or stabbing the top end 22 toward the anchor 26, which allows the anchor 26 to enter the attachment groove 30. The placement guards 31 prevent the anchor 26 from raising out of the attachment groove 30. The attachment groove 30 has a back end 32 and groove extensions 33, which are located adjacent to back end 32 and that are attached to and integral with the sides of the attachment groove 30. The groove extensions 33 are designed to allow the anchor 26 to slide against the back end 32, but prevent the anchor 26 from sliding toward the attachment groove entrance located at the connecting side 27 of the top end 22.

The working side 28 of the top end 22 has a slot 35 that extends from the surface of the working side 28 to the attachment groove 30. The slot 35 has a clip 36, which is connected to the top right edge of the slot 35 and extends diagonally into and across the slot 35. The clip 36 is designed to keep the single dental floss strand 25 within the slot 35.

Figure 11:
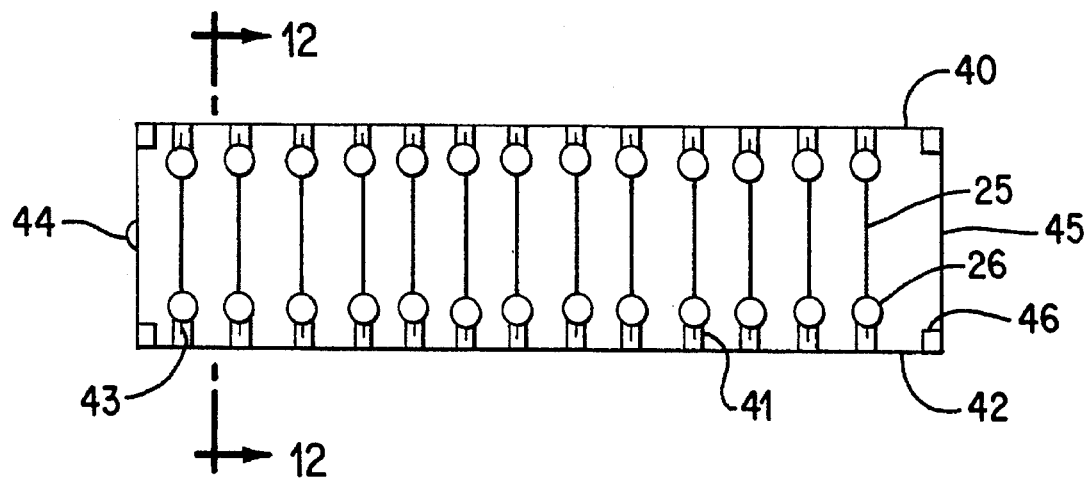
FIG. 11 is a top plan view of a container holding single strands of dental floss.
Figure 12:
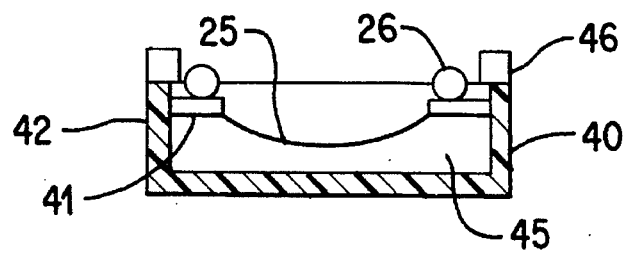
FIG. 12 is a side plan view of a container holding single strands of dental floss taken along lines 12—12 of FIG. 11.
Figure 13:
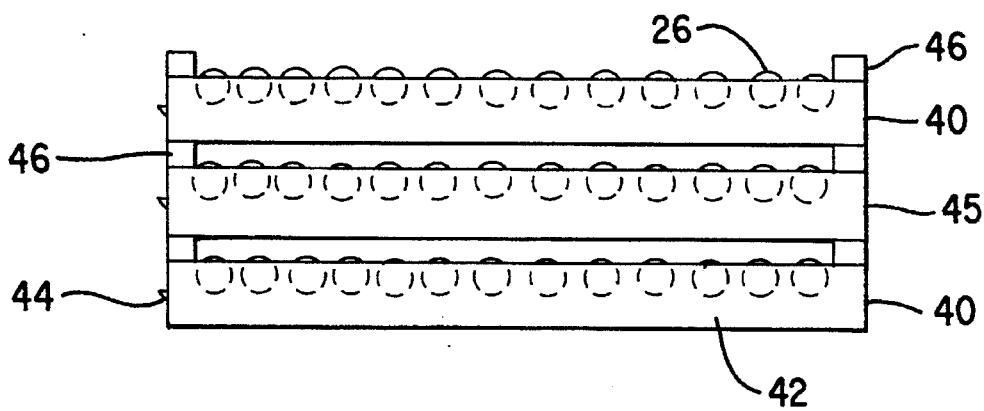
FIG. 13 is a side plan view of several containers stacked together.

As shown in FIGS. 11 and 12, the single dental floss strands 25 are stored in a container 40, which has support notches 41 located on the inner surfaces of sides 42 of the container 40. The support notches 41 can alternatively be attached to the top edges of sides 42. The single dental floss strands 25 are removably inserted through the slots 43 formed within the support notches 41, while the anchors 26 lie on the top surface of the support notches 41. The container 40 also has a floss cutter 44, which is a slightly raised triangular wedge attached to the outer surface of one of the ends 45 of the container 40, but can be of any shape or design. The container 40 can have stacking bars 46 which extend vertically from the top edges of the corners formed by the sides 42 and ends 45. As shown in FIG. 13, through the use of the stacking bars 46, a container 40 can be stacked on a similar container 40 which are then stored within a larger receptacle (not shown) for future use. A container 40 or several stacked containers 40 and the members 21 can be stored in a kit for future use (not shown).

In operation, a user takes both members 21, one in each hand, and stabs the anchors 26 with the top ends 22 of the members 21. The anchors 26 enter into the attachment groove 30 and are held in place by the placement guards 31 and groove extensions 33. The user raises the members 21, which now have the single dental floss strand 25 maintained in the top ends 22, and slightly pulls the members 21 apart to create some tension on the single dental floss strand 25. The single dental floss strand 25 is then engaged and maintained in the slot 35 by the clip 36. The user then manipulates the members 21 into his or her mouth to have the single dental floss strand 25 clean the surfaces in between the teeth. After flossing with the members 21 and the single dental floss strand 25, the user can remove the used single dental floss strand 25 from the members 21, by cutting the single dental floss strand 25 by using the floss cutter 44 and inserting the extricator 24 into the attachment groove 30 of each member 21 and releasing the anchor 26 therein (not shown). The user can discard the used single dental floss strand 25 and rinse the members 21, which are then stored for future use.

It is to be understood that while certain forms of this invention have been illustrated and described, the invention is not limited thereto, except insofar as such limitations are included in the following claims.

What is claimed and described to be secured by Letters Patent is as follows:

1. A dental floss device and applicator assembly comprising:

(a) a pair of separate, substantially elongate members, each of said members having spaced apart top and bottom end portions with a gripping section located between said top and bottom end portions;

(b) a plurality of dental floss segments;

(c) attachment means on each of said top end portion for releasably holding one of said dental floss segments (STRAND) without requiring a user to manipulate with said user's fingers said STRAND to attach said STRAND to said attachment means, said attachment means comprising a slot formed in said top end portion and a groove formed in said top end portion and located adjacent to said slot, said groove having means for releasably holding said STRAND within said groove and guiding said STRAND to said slot, said slot having a first prong protruding from said slot for releasably holding said STRAND within said slot;

(d) a container for storing said dental floss segments and comprising spaced apart opposite sides having a plurality of spaced apart support means attached to said spaced apart opposite sides for releasably holding said dental floss segments, said support means releasing said STRAND from said container when said user presses said top end portion of said members against said STRAND whereby said attachment means releasably holds said STRAND; and (e) said members being of sufficient length to allow said user to insert said members into a person's mouth with said STRAND attached to said top end portion of said members to clean all surfaces of said person's teeth without requiring said user to insert said user's fingers into said person's mouth, said user not having to manipulate said STRAND with said user's fingers when cleaning said person's teeth.

2. A dental floss device and applicator assembly as set forth in claim 1 wherein said dental floss segments are continuous, circular pieces of dental floss.

3. A dental floss device and applicator assembly as set forth in claim 1 wherein said dental floss segments each have spaced apart end portions, with each of said spaced apart end portions having a stationary member.

4. A dental floss device and applicator assembly as set forth in claim 1 wherein said dental floss device and applicator assembly includes a storage receptacle for storing said members and said container when not in use.

5. A dental floss device and applicator assembly as set forth in claim 1 wherein said members are formed of a synthetic plastic material.

6. A dental floss device and applicator assembly as set forth in claim 1 wherein said container has a prong protruding from one of said spaced apart opposite sides for cutting said dental floss segments.

7. A dental floss device and applicator assembly as set forth in claim 1 wherein said container has means for stacking said container on top of a second container, said means for stacking includes a plurality of second prongs extending from said spaced apart opposite sites.

8. A dental floss device and applicator assembly comprising:

(a) a pair of separate, substantially elongate members, each of said members having spaced apart top and bottom end portions with a gripping section located between said top and bottom end portions;

(b) a plurality of dental floss segments, each of said dental floss segments having a continuous, circular configuration;

(c) attachment means on each of said top end portion for releasably holding one of said dental floss segments (STRAND) without requiring a user to manipulate with said user's fingers said STRAND to attach said STRAND to said attachment means, said attachment means comprising a slot formed in said top end portion, a first prong protruding from said slot for releasably holding said STRAND, and an alignment channel means formed in said top end portion and located adjacent to said slot, said alignment channel means for guiding said STRAND under said first prong;

(d) a container for storing said dental floss segments and comprising spaced apart opposite sides having a plurality of spaced apart support means protruding from said spaced apart opposite sides for releasably holding said dental floss segments, said support means releasing said STRAND from said container when said user presses said top end portion of said members against said STRAND whereby said attachment means releasably holds said STRAND; and (e) said members being of sufficient length to allow said user to insert said members into a person's mouth with said STRAND attached to said top end portion of said members to clean all surfaces of said person's teeth without requiring said user to insert said user's fingers into said person's mouth, said user not having to manipulate said STRAND with said user's fingers when cleaning said person's teeth.

9. A dental floss device and applicator assembly as set forth in claim 8 wherein said dental floss device and applicator assembly includes a storage receptacle for storing said members and said container when not in use, said storage receptacle having a means for cutting said dental floss segments.

10. A dental floss device and applicator assembly as set forth in claim 8 wherein said members are formed of a synthetic plastic material.

11. A dental floss device and applicator assembly as set forth in claim 8 wherein said container has a second prong protruding from one of said spaced apart opposite sides for cutting said dental floss segments.

12. A dental floss device and applicator assembly as set forth in claim 8 wherein said container has means for stacking said container on top of a second container, said means for stacking includes a plurality of third prongs extending from said spaced apart opposite sites.

13. A dental floss device and applicator assembly comprising:

(a) a pair of separate, substantially elongate members, each of said members having spaced apart top and bottom end portions with a gripping section located between said top and bottom end portions;

(b) a plurality of dental floss segments, each of said dental floss segments having spaced apart end portions, each of said spaced apart end portions having a stationary member;

(c) attachment means on each of said top end portion for releasably holding one of said dental floss segments (STRAND) without requiring a user to manipulate with said user's fingers said STRAND to attach said STRAND to said attachment means, said attachment means comprising a slot formed in said top end portion and a groove formed in said top end portion and located adjacent to said slot, said groove having means for releasably holding said stationary member within said groove and guiding said STRAND to said slot, said slot having a first prong protruding from said slot for releasably holding said STRAND within said slot;

(d) said bottom end portion having a second prong protruding from bottom end portion for releasing said STRAND from said top end portion of said members;

(e) a container for storing said dental floss segments and comprising spaced apart opposite sides having a plurality of spaced apart support means attached to said spaced apart opposite sides for releasably holding said dental floss segments, said support means releasing said STRAND from said container when said user presses said top end portion of said members against said STRAND and said stationary member enters said groove and said first prong releasably holds said STRAND within said slot whereby said user not having to manipulate said STRAND with said user's fingers when attaching said STRAND to said members; and (f) said members being of sufficient length to allow said user to insert said members into a person's mouth with said STRAND attached to said top end portion of said members to clean all surfaces of said person's teeth without requiring said user to insert said user's fingers into said person's mouth, said user not having to manipulate said STRAND with said user's fingers when cleaning said person's teeth.

14. A dental floss device and applicator assembly as set forth in claim 13 wherein said dental floss device and applicator assembly includes a storage receptacle for storing said members and said container when not in use, said storage receptacle having a means for cutting said dental floss segments.

15. A dental floss device and applicator assembly as set forth in claim 13 wherein said members are formed of a synthetic plastic material.

16. A dental floss device and applicator assembly as set forth in claim 13 wherein said container has a second prong protruding from one of said spaced apart opposite sides for cutting said dental floss segments.

17. A dental floss device and applicator assembly as set forth in claim 13 wherein said container has means for stacking said container on top of a second container, said means for stacking includes a plurality of third prongs extending from said spaced apart opposite sites.

18. A dental floss device and applicator assembly comprising:

(a) a pair of separate, substantially elongate members, each of said members having spaced apart top and bottom end portions with a gripping section located between said top and bottom end portions;

(b) a plurality of dental floss segments, each of said dental floss segments having a continuous, circular configuration;

(c) attachment means on each of said top end portion for releasably holding one of said dental floss segments (STRAND) without requiring a user to manipulate with said user's fingers said STRAND to attach said STRAND to said attachment means;

(d) a container for storing said dental floss segments and comprising spaced apart opposite sides having a plurality of spaced apart support means attached to said spaced apart opposite sides for releasably holding said dental floss segments, said support means releasing said STRAND from said container when said user presses said top end portion of said members against said STRAND whereby said attachment means releasably holds said STRAND; and (e) said members being of sufficient length to allow said user to insert said members into a person's mouth with said STRAND attached to said top end portion of said members to clean all surfaces of said person's teeth without requiring said user to insert said user's fingers into said person's mouth, said user not having to manipulate said STRAND with said user's fingers when cleaning said person's teeth.

19. A dental floss device and applicator assembly as set forth in claim 18 wherein said dental floss device and applicator assembly includes a storage receptacle for storing said members and said container when not in use.

20. A dental floss device and applicator assembly as set forth in claim 18 wherein said members are formed of a synthetic plastic material.

21. A dental floss device and applicator assembly as set forth in claim 18 wherein said container has a prong protruding from one of said spaced apart opposite sides for cutting said dental floss segments and a means for stacking said container on top of a second container, said means for stacking includes a plurality of second prongs extending from said spaced apart opposite sites.

* * * * *